(12) United States Patent
Smiley

(10) Patent No.: US 6,608,003 B2
(45) Date of Patent: Aug. 19, 2003

(54) HERBICIDAL SOLUTIONS COMPRISING FATTY ACID AMMONIUM SALTS AND DICARBOXYLIC ACID DIESTERS AND METHODS OF USING THE SAME

(75) Inventor: Robert A. Smiley, Wilmington, DE (US)

(73) Assignee: Falcon Lab LLC, Wilmington, DE (US)

( * ) Notice: Subject to any disclaimer, the term of this patent is extended or adjusted under 35 U.S.C. 154(b) by 28 days.

(21) Appl. No.: 09/998,743

(22) Filed: Nov. 30, 2001

(65) Prior Publication Data

US 2002/0068680 A1 Jun. 6, 2002

Related U.S. Application Data

(60) Provisional application No. 60/250,421, filed on Dec. 1, 2000.

(51) Int. Cl.$^7$ .......................... A01N 37/02; A01N 37/06
(52) U.S. Cl. .......................... 504/142; 514/547; 514/552
(58) Field of Search .......................... 504/142; 514/547, 514/552

(56) References Cited

U.S. PATENT DOCUMENTS

| | | | |
|---|---|---|---|
| 2,603,560 A | 7/1952 | Stewart | 71/2.3 |
| 2,765,224 A | 10/1956 | Lambrech | 71/2.6 |
| 2,852,426 A | 9/1958 | Stanbury | 167/22 |
| 2,942,023 A | 6/1960 | Gordon et al. | 260/468 |
| 2,948,653 A | 8/1960 | Bavley et al. | 167/22 |
| 3,143,408 A | 8/1964 | Smythe et al. | 71/2.5 |
| 3,399,990 A | 9/1968 | Humphrey et al. | 71/11 |
| 3,555,160 A | 1/1971 | Gier et al. | 424/308 |
| 3,652,653 A | 3/1972 | Emerson et al. | 504/313 |
| 3,810,750 A | 5/1974 | Davidson et al. | 71/78 |
| 3,991,100 A | 11/1976 | Hochberg | 260/485 |
| 4,071,348 A | 1/1978 | Abramitis | 71/78 |
| 4,095,973 A | 6/1978 | Maeda et al. | 71/103 |
| 4,123,552 A | 10/1978 | Kensler, Jr. et al. | 424/311 |
| 4,786,307 A | 11/1988 | Marihart | 71/11 |
| 4,975,110 A | 12/1990 | Puritch et al. | 504/142 |
| 5,035,741 A | 7/1991 | Puritch et al. | 504/142 |
| 5,092,918 A | 3/1992 | Kuchikata | 71/94 |
| 5,098,467 A | 3/1992 | Puritch et al. | 504/142 |
| 5,098,468 A | 3/1992 | Puritch et al. | 504/142 |
| 5,106,410 A | 4/1992 | Puritch et al. | 504/142 |
| 5,196,044 A | 3/1993 | Caulder et al. | 504/127 |
| 5,668,086 A | 9/1997 | Tadayuki et al. | 504/235 |
| 5,683,959 A | 11/1997 | Caulder et al. | 504/127 |
| 5,700,759 A | 12/1997 | Caulder et al. | 504/133 |
| 5,703,019 A | 12/1997 | Evans et al. | 504/320 |
| 5,919,733 A | 7/1999 | Sedun et al. | 504/320 |
| 5,919,734 A | 7/1999 | Jones | 504/320 |
| 5,948,731 A | 9/1999 | Evans et al. | 504/320 |
| 5,994,269 A | 11/1999 | Bugg et al. | 504/127 |
| 6,034,034 A | 3/2000 | Caulder et al. | 504/130 |
| 6,117,823 A | 9/2000 | Smiley | 504/313 |
| 6,136,856 A | 10/2000 | Savage et al. | 514/552 |
| 6,218,336 B1 | 4/2001 | Coleman | 504/118 |
| 6,323,153 B1 | 11/2001 | Smiley | 504/194 |
| 6,323,156 B1 | 11/2001 | Smiley | 504/320 |

FOREIGN PATENT DOCUMENTS

| | | | |
|---|---|---|---|
| CA | 2099631 | 6/1993 | A01N/25/30 |
| DE | 3321529 A1 | 12/1984 | A01N/37/04 |
| DE | 4319263 A1 | 6/1993 | A01N/25/30 |
| GB | 2309904 A | 8/1997 | A01N/25/00 |
| JP | 42006999 | 3/1967 | |

*Primary Examiner*—S. Mark Clardy
(74) *Attorney, Agent, or Firm*—Locke Liddell & Sapp LLP

(57) ABSTRACT

Aqueous compositions containing (i.) a salt of the formula:

$$R_1COO^-X^+ \qquad (I)$$

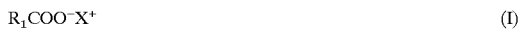

wherein $R_1$ is a $C_7$ to $C_{11}$ hydrocarbyl group and X is ammonium ($NH_4^+$); and (ii.) a diester of the formula:

$$ROOC(CHR_2)_nCOOR' \qquad (II)$$

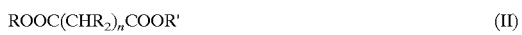

wherein R and R' are independently selected from a $C_1$ to $C_8$ alkyl group, $R_2$ is hydrogen or a $C_1$–$C_3$ alkyl group, and n is from 5 to 12 are highly effective as non-selective herbicides. In a preferred mode, the diesters are soluble in water saturated solutions containing the ammonium salt. The resulting composition can be diluted with water to render a stable emulsion which may be applied as a non-selective herbicide.

35 Claims, No Drawings

HERBICIDAL SOLUTIONS COMPRISING FATTY ACID AMMONIUM SALTS AND DICARBOXYLIC ACID DIESTERS AND METHODS OF USING THE SAME

SPECIFICATION

This application claims priority to provisional application Ser. No. 60/250,421, filed Dec. 1, 2000.

FIELD OF THE INVENTION

The present invention relates to compositions which are highly effective as herbicidal formulations. The compositions are composed of an aqueous solution of an ammonium salt of a carboxylic acid and a dicarboxylic acid diester.

BACKGROUND OF THE INVENTION

Persistent plants that interfere with the growth of desirable plants, such as food crops, ornamentals, turf grass, etc. are known as weeds. For economic and other reasons, mankind has been trying to control the growth of weeds since agriculture first began. One means of weed control has been by the use of chemicals known as herbicides. The sale of herbicides worldwide is in the billions of dollars per year.

There are two major categories of herbicides—selective and non-selective. Selective herbicides only kill selected weeds such as broad leafed plants like dandelion. Exemplary of well-known herbicides is 2,4-D. Non-selective herbicides kill all weeds. Commercially known non-selective herbicides include glyphosate (such as ROUNDUP®) and paraquat. Many of the selective and non-selective herbicides of the prior art are highly toxic. For example, paraquat is a known hazardous material and ROUNDUP often has a higher than desired kill time.

Further, many herbicides, regardless of whether they are selective or non-selective, are toxic to mammals, present complications resulting from buildup in the soil or have other properties which are of concern to health and environmental authorities. Researchers are constantly aiming to overcome some of these concerns.

Recently, it was shown in U.S. Pat. No. 6,323,156, issued on Nov. 27, 2001, that water solutions of ammonium fatty acid salts, such as ammonium pelargonate, function effectively as a non-selective herbicide. Since ammonium pelargonate is derived from naturally occurring pelargonic acid (nonanoic acid) and is non-toxic and biodegradable, it has desirable properties from a safety and environmental standpoint along with its ability to kill weeds. Although being a non-selective herbicide, it is not capable of destroying all weeds.

Further, dimethyl esters of naturally occurring dibasic acids such as azelaic acid, suberic acid and sebacic acid are known to function as non-selective herbicides. These compounds are further non-toxic and biodegradable. Furthermore, they are able to control some weeds that ammonium salts of fatty acids do not. However, since they are completely water insoluble, they are often commercially impractical. For instance, the preparation of a water solution of dimethyl azelate for herbicidal applications requires the use of large amounts of water soluble organic liquids such as acetone or ethanol. In addition to being impractical, such compositions, in light of the water insolubility of the diacid ester, are expensive. Often, such diesters must be applied to the target weed as an emulsion (using inactive emulsifying agents) or as a dispersion (using wettable powders by mixing them with clay). As such, these compositions are more cost prohibitive and less desirable than a water solution. Non-toxic biodegradable herbicides compatible in a water-based formulation are therefore desired.

SUMMARY OF THE INVENTION

Aqueous compositions containing ammonium salts of fatty acids and dicarboxylic acid diesters function remarkably as non-selective herbicides. In the compositions of the invention, the diester of a carboxylic diacid is solubilized in a water solution containing the ammonium salt of a fatty acid, such as ammonium pelargonate. The resulting composition can be diluted with water to render a stable emulsion which may be applied to the locus of unwanted vegetation. Since the mode of action is through the leaves of the vegetation, there is little, if any, residual herbicidal effect in the ground. Thus, it is possible to grow desirable plants adjacent to and around the treated area.

The ammonium salt is a compound of the formula:

$$R_1 COO^- X^+ \qquad (I)$$

wherein $R_1$ is a $C_7$ to $C_{11}$ hydrocarbyl group and X is ammonium ($NH_4^+$). In the formula (I), any of the hydrogen on $R_1$ may be substituted with one or more hydroxyl or a $C_1$–$C_5$ hydrocarbyl group, such as an alkyl group. In a preferred embodiment, the compound of formula (I) is ammonium pelargonate.

Suitable as the dialkyl ester of the dicarboxylic acid are those diesters of the formula:

$$ROOC(CHR_2)_n COOR' \qquad (II)$$

wherein R and R' are independently selected from a $C_1$ to $C_8$ alkyl group, $R_2$ is hydrogen or a $C_1$–$C_3$ alkyl group, and n is from 2 to 10. R and R' on any given compound may be the same or different alkyl group. Highly preferred are those diesters wherein R and R' are the same alkyl group. Particularly desirable esters are the dimethyl esters wherein n is 6 to 8, such as the dimethyl ester of azelaic acid.

DETAILED DESCRIPTION OF PREFERRED EMBODIMENTS

The composition of the invention is a solution containing an ammonium salt and a dicarboxylic acid diester.

The ammonium salt is a compound represented by the formula (I):

$$R_1 COO^- X^+ \qquad (I)$$

wherein $R_1$ is a saturated or unsaturated $C_7$ to $C_{11}$ hydrocarbyl group, X is ammonium ($NH_4^+$), and wherein any of the hydrogen on $R_1$ may be substituted with one or more hydroxyl or $C_1$–$C_5$ hydrocarbyl groups. In a preferred embodiment, the herbicidal composition of the invention contains less than 0.5 wt. % free fatty acid. More preferred, the herbicidal composition contains less than 0.1 wt. % free fatty acid. In a most preferred embodiment, the herbicidal composition of the invention contains essentially no free fatty acid. Preferred as the ammonium salt of formula (I) are the salts of caprylic, pelargonic, capric, undecanoic and lauric acid. The ammonium salt of pelargonic acid is especially preferred.

The dicarboxylic acid diester is a compound represented by the formula (II):

$$ROOC(CHR_2)_n COOR' \qquad (II)$$

wherein R and R' are independently selected from a $C_1$ to $C_8$ alkyl group, $R_2$ is hydrogen or a $C_1$–$C_3$ alkyl group, and n is from 2 to 10. R and R' on any given compound of formula (II) may be the same or different alkyl group. In a preferred embodiment, $R_2$ is hydrogen. In another preferred embodiment, n is between 6 and 8.

Highly preferred as compounds of formula (II) for use in the invention are those wherein R and R' are the same alkyl group, R and R' preferably being a $C_1$ to $C_6$, most preferably a $C_1$ to $C_4$, alkyl group. Particularly desirable esters are the dimethyl, diethyl, disopropyl and dibutyl esters.

The herbicidal composition of this invention may further contain a mixture of two or more of the ammonium salts of formula (I) or two or more of the carboxylic acid diesters of formula (II).

The solution to which is added the carboxylic acid diester generally contains between from about 20 to about 60 weight percent of the ammonium salt of the compound of formula (I). The composition of the invention typically contains between from about 15 to about 28, preferably about 20 to about 25 weight percent of the diester of formula (II). In a preferred embodiment, the composition of the invention comprises a dicarboxylic acid diester of formula (II) dissolved in a saturated solution of the ammonium salt of the fatty acid of formula (I). In order for the water insoluble diester to dissolve in the aqueous salt solution it is preferred to use a saturated salt solution. While one of skill in the art would readily recognize that the solubility of organic compounds in water is decreased by the presence of ions, such as those from water soluble salts, the carboxylic acid diester of formula (II) has been found to be soluble in a relatively saturated solution of an ammonium salt of formula (I). For instance, the composition of the invention may contain, as the dicarboxylic acid diester, dimethyl azelate as high as 23% by weight when a saturated solution of an ammonium salt of formula (I) (containing approximately 40 weight percent of the ammonium salt) is used.

The herbicide is applied as an emulsion to the locus of the unwanted vegetation in an effective amount, i.e. the composition of the invention is diluted with water until an emulsion is formed. Typically, the amount of water added to the composition of the invention to render the emulsion is at a ratio of about 10:1 to about 15:1, such that the amount of carboxylic acid diester in the emulsion is between from about 2.1 to about 1.4 weight percent, which is the preferable range. Any solvent in which the composition may be emulsified may be employed as the diluent.

In a preferred embodiment, a composition of dimethyl azelate (containing methyl esters of other dibasic acids as impurities) in ammonium pelargonate solution is diluted with water to a concentration of each of the active ingredients shown to give good herbicidal results. This is usually about a minimum of about 1 to about 2.5% by weight of ammonium pelargonate and about 0.75 to about 2% by weight dimethyl azelate. Dilution with water to these concentrations gives a milky emulsion which does not separate into an organic phase on standing for periods of 48 hrs. or longer. When a separation does occur, simple shaking or stirring quickly re-establishes the emulsion.

The herbicidal emulsion prepared from the composition of formula (II) in the solution containing formula (I) exhibits several advantages not previously seen with other commercial herbicides. These advantages include:

More Rapid Kill Time. Vegetation usually starts to shrivel and turn color within an hour after receiving a single application. Typically unwanted vegetation is dead in less than 24 hours. Readily obtainable non-toxic herbicides require much longer times. Further, herbicides evidencing quicker kill times in the prior art are toxic.

Based on Naturally Occurring Compounds. The composition of the invention includes compounds found in nature. Few commercially known herbicides are based on naturally occurring compounds.

Action is Through the Leaves. In light of the quick kill time of the herbicidal composition of the invention, reseeding can take place immediately. Most commercial herbicides must be allowed to degrade before reseeding.

Non-toxic and Biodegradable. The herbicidal composition of the invention is non-toxic and further is biodegradable. Many commercial herbicides are hazardous to apply.

Low Cost. The herbicidal composition of the invention are relatively low in cost.

Non-Regulated Solvents.

Since the herbicidal composition of the invention employs non-regulated solvents, one would expect no restrictions on shipping or storage.

The resulting emulsion may be used to control established vegetation in the vicinity of a seeded crop or in a weed concentrate area by contacting the foliage of the unwanted vegetation with the emulsion by spraying or otherwise distributing the composition onto the foliage. Leaves of vegetation sprayed with the herbicidal emulsion usually start to shrivel or turn brown within hours after application. Within 24–48 hours, necrosis is evident. In the case of smaller weeds such as dandelions, chickweed and other common lawn weeds, the roots of the plants also shrivel and turn brown or black within 24 hours.

Spraying is a preferred method of wetting the leaves. Wilting of the plant occurs usually within several hours with necrosis occurring usually within 24 to 48 hours. The higher the concentration of the active ingredients, the faster the weeds are killed. The higher the ambient temperature is at the time of application, the faster the kill time. However, control of some weeds growing from bulbs have been obtained at temperatures as low as 40° F. For instance, cold weather weeds such as star-of-Bethlehem, moneywort and similar weeds may be controlled with the herbicidal emulsion. No commercial herbicides control these bulbous perennials because they are not effective at temperatures below 50° F.

Other weeds and grasses which have been killed by use of the herbicidal emulsion of the invention include quack grass, buttercup, common cinquefoil, multi flora rose, common yellow woodsorrel, prostrate spurge, henbit, poison ivy, poison hemlock, common speedwell, broadleaf plantain, Japanese honeysuckle, dandelion, wild violet, Bermuda grass, nutsedge, wild garlic, knotweed, red sorrel, lambs quarters, pokeweed, carpetweed, crabgrass, buckhorn plantain, nimblewill, or common chickweed. Moss, small tree saplings and suckers and shoots from tree roots and tree stumps may also be controlled with the emulsion.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLES

The following non-limiting examples bring out the more salient features of this invention. All parts are given in terms of weight units except as may otherwise be indicated

Example 1

A mixture of dimethyl esters of dibasic acids is sold commercially by Solutia under the tradename of "Santosolve" and by DuPont as "DBE". These mixtures contain approximately 55–65% dimethyl glutarate (n=3 in formula (II)), 10–25% dimethyl adipate (n=4) and 15–25% dimethyl succinate (n=2). This mixture has a solubility in water of approximately 5% at room temperature.

A 40% solution of ammonium pelargonate was prepared by slowly adding 33 g. of 28% ammonium hydroxide to a stirred mixture of 89.3 g. of nonanoic acid (commercial pelargonic acid from Cognis Corp.) and 124.3 g. of distilled water. The solution was clear and had a pH of 7 as determined by pH paper. To this solution was added with stirring 82.3 g. of DuPont DBE. All of the DBE dissolved to give a clear composition containing 25% DBE, 30% ammonium pelargonate and 45% water.

Example 2

To 361 gm. (2.29 mole) of technical pelargonic acid was added slowly with stirring a solution of 139 gm. of 28% ammonium hydroxide (2.29 mole $NH_3$) in 500 ml. of deionized water. The resultant clear solution (1 kgm.) contained 40% ammonium pelargonate by weight. The pH of the solution as measured by pH paper was 7.

Example 3

Dimethyl pimelate (n=5 in formula (II)) is insoluble in water. By adding successive amounts of dimethyl pimelate (99%) to 100 g. of the 40% ammonium pelargonate prepared in Example 2 it was determined that 22.5 g. of the ester dissolves at 22 deg. to give a clear composition. Thus, a composition containing 17.9% dissolved dimethyl pimelate in aqueous ammonium pelargonate was obtained.

Example 4

Dimethyl suberate (n=6 in formula (II)) is insoluble in water. By adding successive amounts of dimethyl suberate (99%) to 100 g. of the ammonium pelargonate in Example 2 it was determined that 19.3 g. of the ester would dissolve at 22° C. to give a clear composition. Thus, a composition containing 16.2% dissolved dimethyl suberate in aqueous ammonium pelargonate was obtained.

Example 5

A 40% solution of ammonium pelargonate was prepared by slowly adding 33 g. of 28% ammonium hydroxide to a stirred mixture of 89.3 g. of nonanoic acid (commercial pelargonic acid from Cognis Corp.) and 124.3 g. of distilled water. The solution was clear and had a pH of 7 as determined by pH paper. To 100 gm. of the 40% ammonium pelargonate solution was added 30 gm. of technical dimethyl azelate (Cognis Corp.) and the mixture shaken. A clear yellow composition resulted which contained 23% dimethyl azelate, 30.8% ammonium pelargonate and 46.2% water by weight.

Example 6

To 15 ounces (volume) of water was added 1 ounce (volume) of the composition from Example 5. A uniform milky emulsion was obtained which did not separate on standing at room temperature.

Example 7

The emulsion from Example 6 was sprayed from a handheld spray bottle on a variety of weeds and grasses including dandelion, wild onion, nimblewill, fescue, wild violet, Japanese honeysuckle, crabgrass and others. All of the wetted plants wilted and turned brown within 48 hours. None of them grew back.

Example 8

To 10 ounces (volume) of water was added 1 ounce (volume) of the composition from Example 5. A uniform milky emulsion was obtained. This emulsion was sprayed selectively on star-of-Bethlehem plants growing in turf. The ambient temperature was 40° F. Within 24 hrs, the treated plants had turned brown and shriveled. Within a week, they appeared completely dead. The treated plants did not grow back the following year.

Example 9

A pint of a solution prepared by the procedure of Example 5 was added to 5 quarts of water (1/10 dilution). The milky emulsion that resulted was sprayed from a tank sprayer on a large patch of blooming moneywort. The temperature at the time of spraying was 48° F. The leaves of the treated moneywort turned yellow within 48 hrs. After a week, the plants had decomposed. There was no regrowth the following year.

From the foregoing, it will be observed that numerous variations and modifications may be effected without departing from the true spirit and scope of the novel concepts of the invention.

What is claimed is:

1. A composition comprising a saturated solution of at least one compound represented by the formula:

wherein $R_1$ is a $C_7$ to $C_{11}$ hydrocarbyl group, optionally substituted with one or more hydroxyl or $C_1$–$C_5$ hydrocarbyl groups, and X is ammonium in which is dissolved a carboxylic acid diester of the formula:

wherein R and R' are independently selected from a $C_1$ to $C_8$ alkyl group, $R_2$ is hydrogen or a $C_1$–$C_3$ alkyl group and n is from 5 to 12.

2. The composition of claim 1, wherein the amount of the compound of formula (I) in the solution is between from about 20 to about 60 weight percent.

3. The composition of claim 1, wherein the amount of the compound of formula (II) in the composition is between from about 15 to about 28 percent by weight.

4. The composition of claim 1, wherein the compound of formula (I) is the ammonium salt of caprylic, pelargonic, capric, undecanoic, or lauric acid.

5. The composition of claim 4, wherein the compound of formula (I) is ammonium pelargonate.

6. The composition of claim 2, wherein the amount of the compound of formula (I) in the saturated solution is about 40 weight percent.

7. The solution of claim 1, wherein $R_2$ is hydrogen and further wherein n is 6 to 8.

8. The composition of claim 6, wherein the compound of formula (I) is ammonium pelargonate.

9. The solution of claim 8, wherein the compound of formula (II) is dimethyl azelate.

10. The solution of claim 1, wherein $R_1$ is a saturated hydrocarbyl group.

11. An herbicidal emulsion comprising a diluted composition of a solution of at least one compound represented by the formula:

$$R_1COO^-X^+ \quad (I)$$

wherein $R_1$ is a $C_7$ to $C_{11}$ hydrocarbyl group, optionally substituted with one or more hydroxyl or $C_1$–$C_5$ hydrocarbyl groups; and X is ammonium and a carboxylic acid diester of the formula:

$$ROOC(CHR_2)_nCOOR' $$

wherein R and R' are independently selected from a $C_1$ to $C_8$ saturated alkyl group, $R_2$ is hydrogen or a $C_1$–$C_3$ alkyl group, and n is from 5 to 12.

12. The emulsion of claim 11, wherein the compound of formula (I) is the ammonium salt of caprylic, pelargonic, capric, undecanoic, or lauric acid.

13. The emulsion of claim 12, wherein the compound of formula (I) is ammonium pelargonate.

14. The emulsion of claim 12, wherein $R_2$ is hydrogen and further wherein n is from 6 to 10.

15. The emulsion of claim 14, wherein the compound of formula (II) is dimethyl azelate.

16. The emulsion of claim 11, wherein $R_1$ is a saturated hydrocarbyl group.

17. A method for the prevention or elimination of undesired vegetation which comprises applying to the locus of the undesired vegetation a herbicidally effective amount of a composition comprising (i) a solution of at least one compound represented by the formula:

$$R_1COO^-X^+ \quad (I)$$

wherein $R_1$ is a $C_7$ to $C_{11}$ hydrocarbyl group, optionally substituted with one or more hydroxyl or $C_1$–$C_5$ hydrocarbyl groups and X is ammonium; and (ii) a carboxylic acid diester of the formula:

$$ROOC(CHR_2)_nCOOR'$$

wherein R and R' are independently selected from a $C_1$ to $C_8$ saturated alkyl group, $R_2$ is hydrogen or a $C_1$–$C_3$ alkyl group, and n is 5 to 12.

18. The method of claim 17, wherein the composition comprises a solution of a compound of formula (I) in which is dissolved a carboxylic acid diester of formula (II).

19. The method of claim 18, wherein the amount of the compound of formula (I) in the solution is about 40 weight percent.

20. The method of claim 17, wherein the amount of the compound of formula (II) in the composition is between from about 15 to about 28 percent by weight.

21. The method of claim 18, wherein the solution of (ii) is a saturated solution.

22. The method of claim 17, wherein the compound of formula (I) is ammonium pelargonate.

23. The method of claim 17, wherein n is from 6 to 8.

24. The method of claim 23, wherein the compound of formula (II) is dimethyl azelate.

25. A method of controlling plant growth which comprises applying to a plant a herbicidally effective amount of an aqueous emulsion of a composition of a solution of at least one compound represented by a formula:

$$R_1COO^-X^+ \quad (I)$$

wherein $R_1$ is a $C_7$ to $C_{11}$ hydrocarbyl group, optionally substituted with one or more hydroxyl or $C_1$–$C_5$ hydrocarbyl coups, and X is ammonium in which is dissolved in said solution a carboxylic acid diester of the formula:

$$ROOC(CHR_2)_nCOOR' \quad (II)$$

wherein R and R' are independently selected from a $C_1$ to $C_8$ saturated alkyl group, $R_2$ is hydrogen or a $C_1$–$C_3$ alkyl group, and n is from 5 to 12.

26. The method of claim 25, wherein the amount of the compound of formula (II) in the composition is between from about 15 to about 28 percent by weight.

27. The method of claim 25, wherein the compound of formula (I) in the solution is between from about 20 to about 60 weight percent.

28. The method of claim 27, wherein the amount of the compound of formula (I) in the solution is about 40 weight percent.

29. The method of claim 25, wherein the solution containing the compound of formula (I) is a saturated solution.

30. The method of claim 29, wherein the compound of formula (I) is ammonium pelargonate.

31. The method of claim 29, wherein $R_2$ is hydrogen and further wherein n is 6 to 10.

32. The method of claim 31, wherein the compound of formula (II) is dimethyl azelate.

33. The method of claim 29, wherein $R_1$ is a saturated hydrocarbyl group.

34. The method of claim 25, wherein the weight ratio of water in the aqueous emulsion to the composition is between from about 10:1 to about 15:1.

35. The method of claim 29, wherein the weight ratio of water in the aqueous emulsion to the composition is between from about 10:1 to about 15:1.

* * * * *